United States Patent
Wang et al.

(10) Patent No.: US 7,985,879 B2
(45) Date of Patent: Jul. 26, 2011

(54) PROCESS FOR MAKING GALANTAMINE

(75) Inventors: Lunghu Wang, Kaohsiung (TW); Yung Fa Chen, Tainan County (TW); Julian Paul Henschke, Harlow (GB)

(73) Assignee: Scinopharm Taiwan Ltd., Tainan County (TW)

( * ) Notice: Subject to any disclaimer, the term of this patent is extended or adjusted under 35 U.S.C. 154(b) by 414 days.

(21) Appl. No.: 12/080,380

(22) Filed: Apr. 2, 2008

(65) Prior Publication Data

US 2008/0255347 A1 Oct. 16, 2008

Related U.S. Application Data

(60) Provisional application No. 60/923,191, filed on Apr. 12, 2007.

(51) Int. Cl.
*C07C 231/02* (2006.01)
(52) U.S. Cl. .................. 564/142; 564/138; 540/576
(58) Field of Classification Search .................. 564/138, 564/142; 540/576
See application file for complete search history.

(56) References Cited

FOREIGN PATENT DOCUMENTS

WO  WO 96/40751 A1  12/1996

OTHER PUBLICATIONS

Marco-Contelles, et al., Synthesis and Pharmacology of Galantamine, *Chem. Rev.* 2006, 106, 116-133.
T. Kametani, et al., Studies on the Synthesis of heterocyclic Compounds. Part CCCXV. Modified Total Synthesis of (±)-Galanthamine through Phenol Oxidation, J. Chem. Soc. (C), p. 2603-2605, 1969.
T. Kametani, et al., Modified Total Synthesis of (±)-Galanthamine through Phenol Oxidation, *Chemical Communications*, 1969, p. 425-426.
T. Kametani, et al., Studies of Synthesis of Heterocyclic Compounds. Part DVII(1). A Synthesis of (±)-N-Norgalanthamine, Feb. 1973, p. 35-37.
Marco et al., Galanthamine, a Natural Product for the Treatment of Alzheimer's Disease, *Recent Patents on CNS Drug Discovery* 2006, 1(1):105-111.
Montalbetti et al., Amid Bond Formation and Peptide Coupling, *Tetrahedron* 2005, 61:10827-10852-10852.

*Primary Examiner* — Shailendra Kumar
(74) *Attorney, Agent, or Firm* — Cohen Pontani Lieberman & Pavane LLP

(57) ABSTRACT

A novel process for the preparation of N-methyl-N-(2-[4-hydroxyphenyl]ethyl)-5-hydroxy-4-methoxy benzene carboxamide, which is useful as an intermediate in the synthesis of (−)-galantamine, comprises the reaction of a 5-hydroxy-4-methoxy benzoic acid derivative with N-methyl-N-(2-[4-hydroxyphenyl]ethyl) amine.

26 Claims, No Drawings

PROCESS FOR MAKING GALANTAMINE

RELATED APPLICATIONS

This application claims priority from U.S. Provisional Patent Application Ser. No. 60/923,191 which was filed on Apr. 12, 2007.

BACKGROUND OF THE INVENTION

1. Field of the Invention

The present invention relates to a novel synthesis of (−)-galantamine and N-methyl-N-(2-[4-hydroxyphenyl]ethyl)-5-hydroxy-4-methoxy benzene carboxamide, which is a key intermediate for the synthesis of (−)-galantamine, a drug approved for Alzheimer disease.

2. Description of the Related Art

N-methyl-N-(2-[4-hydroxyphenyl]ethyl)-2-bromo-5-hydroxy-4-methoxy benzene carboxamide (C2) is an important intermediate for (−)-galantamine synthesis. See, e.g., the following references:
(1) Kametani, T.; Yamaki, K.; Yagi, H.; Fukumoto, K. *J. Chem. Soc., Chem. Commun.* 1969, 425.
(2) Kametani, T.; Yamaki, K.; Yagi, H.; Fukumoto, K. *J. Chem. Soc.* (C) 1969, 2602.
(3) Kametani, T.; Shishido, K.; Hayashi, E.; Seino, C.; Kohno, T.; Shibuya, S.; Fukumoto, K. *J. Org. Chem.* 1971, 36, 1295.
(4) Kametani, T.; Yamaki, K.; Terui, T. *J. Heterocycl. Chem.* 1973, 10, 35.
(5) Kametani, T.; Premila, M. S.; Fukumoto, K. *Heterocycles* 1976, 4, 111.
(6) José Marco-Contelles, Maria do Carmo Carreiras, Carolina Rodríguez, Mercedes Villarroya, and Antonio G. García; *Chem. Rev.* 2006, 106, 116-133.

The entire content of each of the above references is incorporated herein by reference.

The general processes disclosed in the art for the preparation of N-methyl-N-(2-[4-hydroxyphenyl]ethyl)-2-bromo-5-hydroxy-4-methoxy benzene carboxamide (C2) is based on coupling 2-bromo-5-benzyloxy-4-methoxy benzoic acid (B4) and N-methyl-N-2-(4-benzyloxyphenyl)ethyl amine (A3) followed by de-protection of the benzyl ether with hydrobromic acid. (see Kametani, et. al., *J. Chem. Soc.* (C) 1969, 2602). As shown in Scheme I, there are nine steps in the synthesis of the title compound.

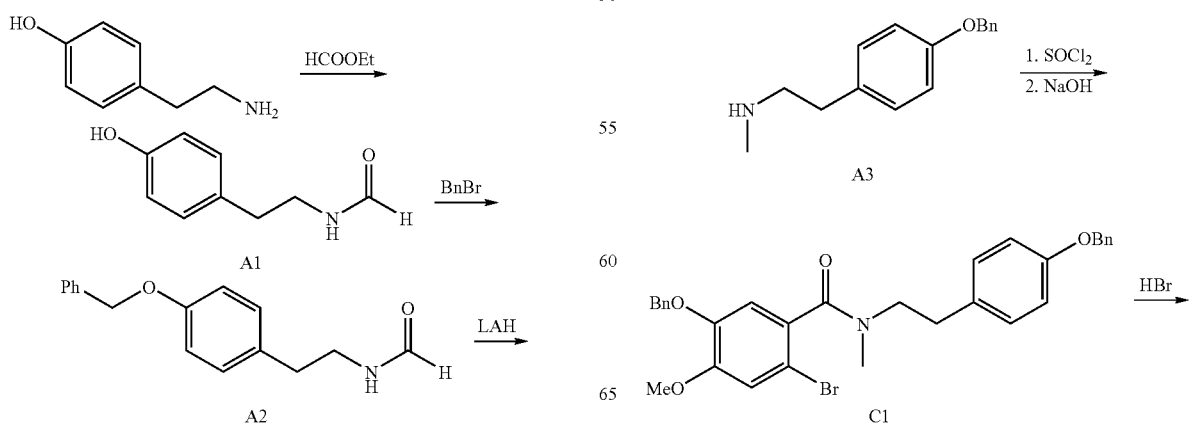

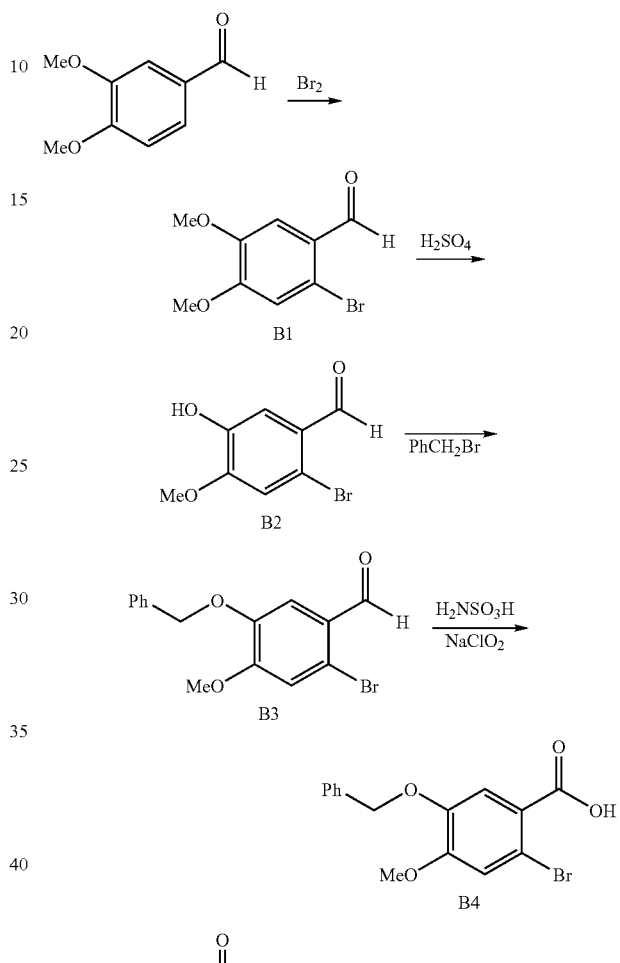

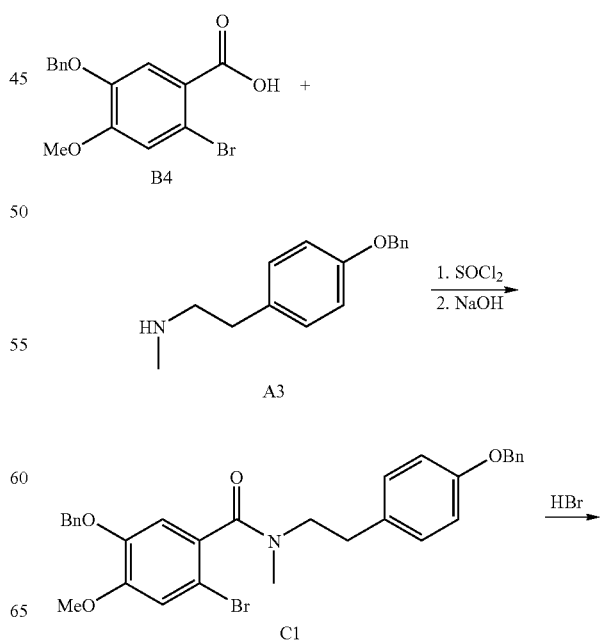

-continued

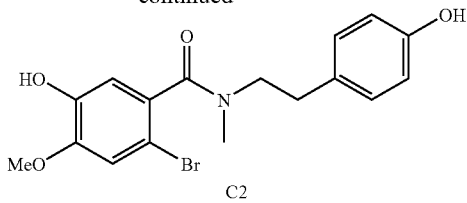
C2

Specifically, the nine steps as shown in Scheme I are:

1) Tyramine is formulated with a mixture of ethyl formate and formic acid in THF to give amide A1.

2) Amide A1 is benzylated with benzyl bromide and potassium carbonate in DMF to obtain compound A2.

3) Compound A2 is reduced by lithium aluminum hydride in THF to give amine A3.

4) Bromination of 3,4-dimethoxybenzaldehyde using bromine in methanol to afford 2-bromo-4,5-dimethoxybenzaldehyde (B1).

5) Compound B1 is demethylated in concentrated sulfuric acid to give 2-bromo-5-hydroxy-4-methoxybenzaldehyde (B2).

6. B2 is benzylated with benzyl bromide and potassium carbonate in DMF to obtain 5-benzyloxy-2-bromo-4-methoxybenzaldehyde (B3).

7) Compound B3 is oxidized with sodium chlorite and sulfamic acid in isopropanol to give acid B4.

8) Compound B4 is reacted with thionyl chloride in dichloromethane to give its corresponding acid chloride which is coupled with A3 in the presence of 3 N NaOH in dichloromethane to formamide C1.

9) Compound C1 is debenzylated with ethanolic hydrobromic acid to give desired product C2.

The synthesis of C2 as shown in Scheme I takes a number of steps and results in relatively low and inconsistent yields of the desired product. The removal of both benzyl ether protecting groups by hydrobromic acid gives a major impurity C3 (formula shown below) resulting from benzyl migration to the phenol ring. This impurity proves to be very difficult to remove from the product.

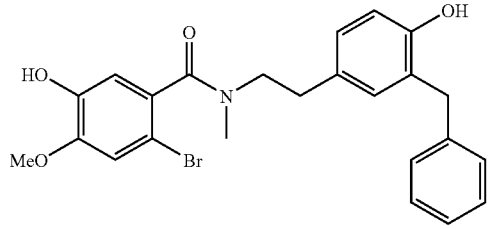
C3

Therefore, there is a need for the development of a process for the preparation of N-methyl-N-(2-[4-hydroxyphenyl]ethyl)-2-bromo-5 hydroxy-4-methoxy benzene carboxamide (C2) via a simple, short, relatively inexpensive and highly efficient synthesis.

SUMMARY OF THE INVENTION

Accordingly, the present invention provides a practical and economical process for the preparation of a N-methyl-N-(2-[4-hydroxyphenyl]ethyl)-5-hydroxy-4-methoxy benzene carboxamide derivative of formula I

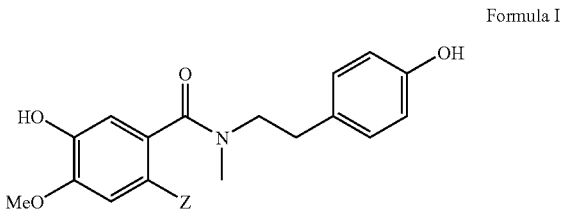
Formula I wherein Z is a blocking group such as halogen or t-butyl. Preferably, Z is bromo or chloro. The compound of formula I can be used as an intermediate for preparing (−)-galantamine.

When Z is bromo, the compound of formula I is N-methyl-N-(2-[4-hydroxyphenyl]ethyl)-2-bromo-5-hydroxy-4-methoxy benzene carboxamide (C2).

In accordance with the present invention, the compound of Formula I is prepared by direct coupling the compound of Formula III

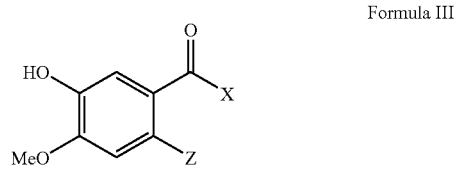
Formula III wherein X is a leaving group, with N-methyl-N-(2-[4-hydroxyphenyl]ethyl) amine or an acid salt thereof.

The compound of Formula III can be prepared by activating a compound of Formula II:

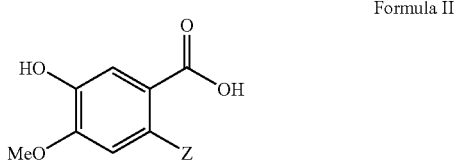
Formula II wherein Z is defined as above, with a coupling agent to give an activated compound of the formula III:

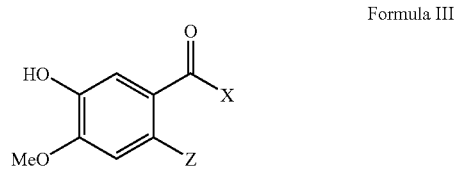
Formula III wherein X is a leaving group resulting from the use of the coupling agent.

This method is readily amenable to scale-up, uses cost-effective and readily available reagents, and is therefore capable of practical application to large scale manufacture. In accordance with the present invention, the compound of Formula I may be made in relatively high yield and purity.

The compound of Formula I may be used as an intermediate to make (−)-galantamine by any suitable method including those known in the art (see the above-mentioned references or U.S. Pat. No. 6,271,371, the entire content of this patent is incorporated herein by reference.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described the preferred embodiments of the invention.

DETAILED DESCRIPTION OF THE PRESENTLY PREFERRED EMBODIMENTS

As an embodiment, the following is provided to describe the process of making N-methyl-N-(2-[4-hydroxyphenyl]ethyl)-2-bromo-5-hydroxy-4-methoxy benzene carboxamide (C2) of the formula:

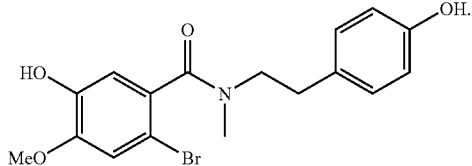

It should be noted that Br in the above formula C2 can be replaced by any other suitable blocking group, such as chloro and t-butyl.

An embodiment of the general process for the preparation of N-methyl-N-(2-[4-hydroxyphenyl]ethyl)-2-bromo-5-hydroxy-4-methoxy benzene carboxamide (C2) comprises:

(1) activating a compound 2-bromo-5-hydroxy-4-methoxy benzoic acid (B13) of the formula:

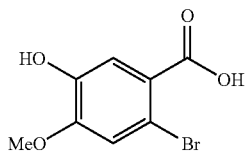

with a coupling agent to give a compound of the formula:

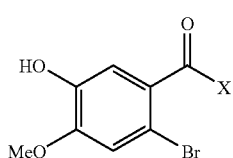

wherein X in the B13X formula represents a leaving group; and (2) coupling such activated compound with a compound N-methyl-N-(2-[4-hydroxyphenyl]ethyl) amine (A12) of the formula:

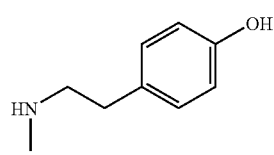

or an acid salt thereof in the presence of a base to give a compound of the formula:

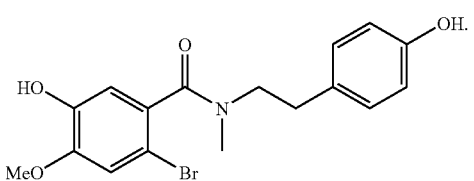

The acid salt of compound A12 is preferably HCl or HBr salt.

Preferably, the carboxyl group of compound of B13 is activated via reaction with a halogenating agent to provide derivatives substituted with F, Cl, Br, or I; or alternatively trichloroacetonitrile to provide the corresponding trichloroimidate (=C(NH)CCl$_3$); or an optionally substituted alkyl or aryl acid halide or acid anhydride to provide the corresponding optionally substituted anhydride such as —O—CO—R or —O—COCF$_3$ or —O—COCCl$_3$ wherein R is substituted or unsubstituted C$_1$-C$_6$ alkyl, substituted or unsubstituted phenyl; or alternatively an optional substituted alkyl or aryl alkoxide to provide the corresponding optionally substituted ester —O—R wherein R is a C$_1$-C$_6$ alkyl, substituted C$_1$-C$_{16}$ alkyl, substituted or unsubstituted phenyl group; or alternatively, an N-hydroxy amide, such as N-hydroxy succinimide (HOSu), or hydroxyl benzotriazole, such as N-hydroxy-benzotriazole (HOBt) and 1-hydroxy-7-azabenzotriazole (HOAt), which is commonly used in peptide synthesis to provide the corresponding N-hydroxy amide ester. Likewise, the leaving group X is preferably halogen, trichloroimidate (—C(NH)CCl$_3$), —O—CO—R, —O—COCF$_3$, —O—COCCl$_3$; —O—R, —Osu, —OBt, or —OAt, wherein R is a substituted or unsubstituted C$_1$-C$_6$ alkyl group, substituted or unsubstituted phenyl group.

More preferably, the coupling agent in step (1) is thionyl chloride to provide the corresponding acid chloride of compound of B13.

Preferably, step (1) is carried out in an organic solvent. The organic solvent is preferably ethyl acetate (EtOAc), methylisobutyl ketone (MIBK), toluene, tetrahydrofuran (THF), diethyl ether, diglyme, methyl t-butyl ether (MTBE), methylene chloride (CH$_2$Cl$_2$), or any mixture thereof. More preferably, the organic solvent used in the step (1) is ethyl acetate (EtOAc).

Preferably, the activation of step (1) is carried out at about 45 to 50° C. and is followed by vacuum distillation to remove the excess, unreacted coupling agent such as thionyl chloride.

In step (2) it is preferred that the coupling of activated B13X is allowed to react with A12 in a solvent in the presence of a base. It should be noted that the base does not have to be used, when the blocking group in compound of Formula I is not halogen, such as bromo. The solvent is typically an organic solvent which is preferably selected from methylene chloride (CH$_2$Cl$_2$), methanol (MeOH), ethanol (EtOH), isopropanol (IPA), methylisobutyl ketone (MIBK), toluene, tetrahydrofuran (THF), diethyl ether, diglyme, and methyl t-butyl ether (MTBE), and mixtures thereof. The mixture of methylene chloride (CH$_2$Cl$_2$) and methanol (MeOH) is a preferred solvent system. Typically, the base is an alkali hydroxide. Alternatively, the base can be a tertiary amine base. The coupling can also be carried out in a two phase system with an organic solvent and an aqueous base of alkali hydroxide or alkali carbonate. It is more preferred to carry out the reaction in a mixture of methylene chloride (CH$_2$Cl$_2$) and methanol (MeOH) with sodium hydroxide as the base. The reaction is typically carried out at a temperature of about 0-50° C. When the mixture of methylene chloride and methanol is used as solvent, and sodium hydroxide is used as a base, the preferred reaction temperature is about 0 to 5° C.

2-bromo-5-hydroxy-4-methoxy benzoic acid (B13) used in step (1) can be prepared by any suitable method including those known in the art. As an example, the compound can be obtained in accordance with the following synthetic scheme II.

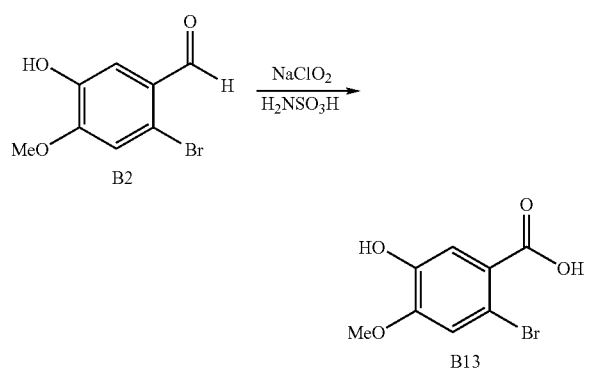

2-Bromo-5-hydroxy-4-methoxy benzaldehyde (B2), available from processes described in the literature, can be oxidized to the corresponding carboxylic acid by sodium chlorite in the presence of sulfamic acid in high yield.

Likewise, N-methyl-N-(2-[4-hydroxyphenyl]ethyl) amine (A12) used in step (2) can be obtained by any suitable method such as a method known in the art. As an example, compound A12 can be made in accordance with the synthetic scheme III.

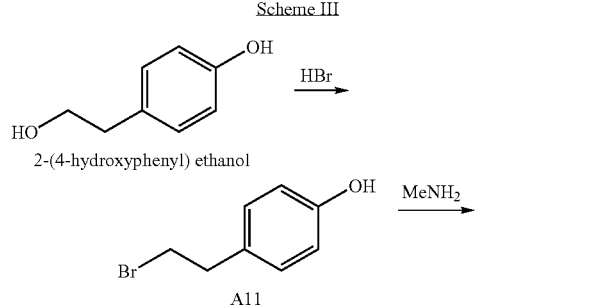

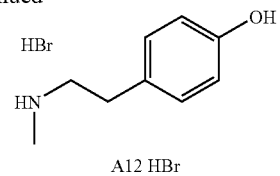

2-(4-hydroxyphenyl) ethanol is converted to the corresponding 2-(4-hydroxyphenyl)ethyl chloride or bromide on reacting with concentrated aqueous hydrochloric acid or hydrobromic acid, respectively. Amination of the 2-(4-hydroxyphenyl)ethyl chloride or bromide is effectively conducted with a large excess of aqueous methylamine solution or an organic solution of methylamine. Organic solvents inert to amination can be used for the reaction. The preferred organic solvent is a low boiling alcohol solvent such as methanol (MeOH), ethanol (EtOH), isopropanol (IPA), n-butanol, and sec-butanol.

The starting materials and reagents for the subject processes are either commercially available, known in the literature, or may be prepared following literature methods described for analogous compounds. The intermediate or final product involved in the present process may be purified by crystallization, distillation, normal phase or reverse phase chromatography, or combination of any of these technique.

The following examples are provided for the purpose of further illustration only and are not intended to be limitations on the disclosed invention.

EXAMPLE 1

(2-[4-hydroxyphenyl]ethyl) bromide (A11)

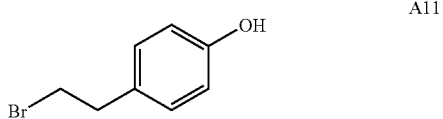

500 g 2-(4-hydroxyphenyl) ethanol was placed in a 5 L round bottom flask, to which 2960 g of 48% aq. HBr was added with stirring. The reaction mixture was placed in a bath at 75° C. After 2.5 h agitation 5 g of A11 seed crystals was added. The reaction mixture was stirred at this temperature for another 24 h. The reaction mixture was slowly cooled to 20° C. The precipitate was isolated by filtration and washed with 10% aq. sodium bicarbonate solution to give 700 g (96% yield) of the title product. $^1$H NMR (CDCl$_3$); δ 3.10 (2H, t, J=7.8 Hz), 3.53 (2H, t, J=7.5 Hz), 6.80 (2H, d, J=8.4 Hz), 7.09 (2H, d, J=8.4 Hz).

(2-[4-hydroxyphenyl]ethyl)chloride

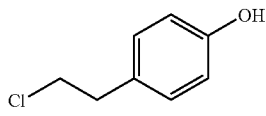

In a similar process using 12N HCl, 2-(4-hydroxyphenyl) ethanol gave 70% isolated yield of the (2-[4-hydroxyphenyl]

ethyl) chloride. $^1$H NMR (CDCl$_3$) δ 2.96 (2H, t, J=7.8 Hz), 3.67 (2H, t, J=7.2 Hz), 6.79 (2H, d, J=8.4 Hz), 6.94 (2H, d, J=8.1 Hz)

EXAMPLE 2

N-methyl-N-(2-[4-hydroxyphenyl]ethyl) amine HBr (A12 HBr)

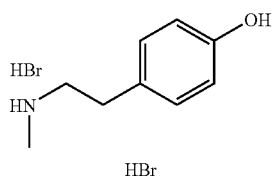

1000 mL of IPA was placed in a 3 L flask and cooled to 0° C. A steady stream of methylamine gas from a cylinder was slowly passed through the IPA until the total volume reached 1750 ml. 100 g of (2-[4-hydroxyphenyl]ethyl) bromide (A11) was added to the cooled methylamine IPA solution in several portions. The cooling bath was removed after all A11 was added. The reaction mixture was allow to warm to room temperature and continue to stir for another 10-12 h. The excess methylamine was distilled into another 1000 mL of pre-cooled to 0° C. IPA by heating the reaction mixture at 50° C. When most of the methylamine was distilled off, the bath temperature was raised to 100° C. and the IPA was distilled out. After most of the IPA had been distilled out, about 300 mL of IPA was added to the reaction mixture and distillation was continued to aid removal of the methylamine. After the volume was reduced to 250 mL, the reaction mixture was allowed to cool down to room temperature. The precipitate was collected by filtration and washed by toluene to give 104 g (90% yield) of N-methyl-N-(2-[4-hydroxyphenyl]ethyl) amine as an HBr salt (A12 HBr). $^1$H NMR (CDCl$_3$) δ 2.69 (3H, s, CH$_3$), 2.90 (2H, t, J=7.2 Hz), 3.18 (2H, t, J=6.3 Hz), 6.76 (2H, d, J=8.7 Hz), 7.11 (2H, d, J=8.7 Hz)

EXAMPLE 3

2-bromo-5-hydroxy-4-methoxy benzoic acid (B13)

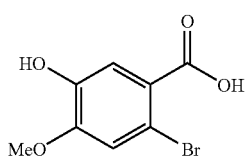

1 Kg of 2-bromo-5-hydroxy-4-methoxy benzaldehyde (B2) and 1.255 Kg of sulfamic acid were added with stirring into a mixture of 4.473 Kg of EtOAc and 8 L of water. The reaction mixture was stirred until all of the solid had dissolved. The reaction mixture was cooled to between −10 and 0° C. An aqueous solution of sodium chlorite was prepared by dissolving 505 g of sodium chlorite in 3 L of water. The sodium chlorite solution was added to the pre-cooled B2 solution at a rate that maintained the reaction temperature under 5° C. After the complete addition of sodium chlorite solution, the reaction mixture was stirred for another hour at 0° C. and was then allowed to warm up to room temperature. The reaction was monitored by TLC. After the TLC analysis showed completion of the reaction, the aqueous layer was separated. The aqueous layer was extracted with EtOAc (1.789 Kg) and the combined organic layer was transferred to another flask and EtOAc was removed by vacuum distillation at 40° C. 6.92 Kg of toluene was added at between 30 to 40° C., the slurry was cooled to between −10 to 0° C. and the precipitate was collected by filtration to give about 950 g (89% (yield) of 2-bromo-5-hydroxy-4-methoxy benzoic acid (B13). $^1$H NMR (CDCl$_3$) δ 3.95 (3H, s, CH$_3$), 7.22 (1H, s, CH), 7.46 (1H, s, CH).

EXAMPLE 4

N-methyl-N-(2-[4-hydroxyphenyl]ethyl)-2-bromo-5-hydroxy-4-methoxy benzene carboxamide (C2)

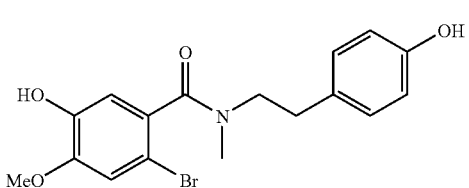

Method 1

A mixture of 2-bromo-5-hydroxy-4-methoxy benzoic acid (B13) (1.49 kg by purity), DMF (0.071 kg) and EtOAc (6.712 kg) was stirred and heated to about 45 to 50° C. under an atmosphere of nitrogen. To this was slowly added thionyl chloride (1.29 Kg) whilst maintaining the temperature at between 45 to 50° C. This was then stirred for about 1 hour. Thus formed 2-bromo-5-hydroxy-4-methoxy benzoyl chloride solution was concentrated under vacuum, cooled to about 30° C. and was then diluted with dichloromethane (9.95 kg) under an atmosphere of nitrogen.

In a separate reaction vessel, a mixture of sodium hydroxide (0.603 Kg) and methanol (3.18 Kg) was stirred until the sodium hydroxide was completely dissolved and then N-methyl-N-(2-[4-hydroxyphenyl]ethyl) amine HBr salt (A12 HBr) (1 kg, by assay) in methanol (1.58 Kg) was added under an atmosphere of nitrogen. After stirring, the above mixture was concentrated to provide N-methyl-N-(2-[4-hydroxyphenyl]ethyl) amine as a slurry. The solution was cooled to about 5° C. under an atmosphere of nitrogen and then stirred for about 0.5 hours.

The previously prepared 2-bromo-5-hydroxy-4-methoxy benzoyl chloride (B13-Cl) in dichloromethane solution was transferred into the slurry of N-methyl-N-(2-[4-hydroxyphenyl]ethyl) amine at about 5° C. and then stirred for about 0.5 hours under an atmosphere of nitrogen. The solution was concentrated under vacuum and then cooled to between 25 to 35° C. To this was then added a 15% w/v solution of NaOH in methanol (0.173 Kg sodium hydroxide in methanol 0.910 Kg) and was then heated to between 25 to 35° C. The solution was stirred for about 8 hours and then the pH was adjusted to between 2 to 5 with 32% hydrochloric acid (~0.6 Kg). The solution was concentrated and the residue was cooled to about 30° C. Dichloromethane (6.628 Kg) and water (15 Kg) were added into the above mixture and then cooled to about 5° C. and was then stirred for about 2 hours. The solidified product was filtered and washed twice with dichloromethane (0.663

Kg each) to provide crude N-methyl-N-(2-[4-hydroxyphenyl]ethyl)-2-bromo-5-hydroxy-4-methoxy benzene carboxamide (C2).

The crude product (1 kg) was heated under reflux in methanol (3.164 Kg) with activated carbon (0.05 kg) for about 1 hour. The mixture was filtered through celite which was then washed with methanol. The solution was concentrated under vacuum and cooled to about 25° C. To this was added dichloromethane (6.628 Kg) followed by stirring for about 15 minutes. Water was added (15 Kg) and the mixture was stirred for 0.5 hours and was then cooled to between 0 to 10° C. and stirred for about 2 hours. The slurry was filtered and washed with dichloromethane (1.326 Kg) and dried under vacuum at about 80° C. for 12 hours to provide purified N-methyl-N-(2-[4-hydroxyphenyl]ethyl)-2-bromo-5-hydroxy-4-methoxy benzene carboxamide (C2) useful for conversion into (−)-galantamine. $^1$H NMR (d$_6$-DMSO) δ 2.56 (2H, t, J=7.5 Hz), 2.75 (1.5H, NCH$_3$, s), 2.99 (1H, NCH$_2$, t, J=6.0 Hz), 3.13 (1.5H, NCH$_3$, s), 3.36 (1H, NCH$_2$, t, J=6.9 Hz), 3.60 (1.5H, s), 3.61 (1.5H, s), 6.32 (0.5H, s), 6.39 (0.5H, s), 6.42 (1H, d, J=8.7 Hz), 6.50 (1H, d, J=8.7 Hz), 6.58 (1H, d, J=8.1 Hz), 6.87 (1H, d, J=8.4 Hz), 6.91 (0.5H, s), 6.92 (0.5H, s), 9.00 (1H, s), 9.31 (0.5H, s), 9.37 (0.5H, s).

Method 2

To a solution of 138 g 2-bromo-5-hydroxy-4-methoxy benzoic acid (B13) in MIBK (690 mL) was added thionyl chloride (106 g) and DMF (13 mL) and the reaction mixture was heated to 80° C. and stirred at this temperature until TLC analysis indicated the complete disappearance of B13. The resulting mixture was subjected to distillation to remove the excess thionyl chloride. After distillation of thionyl chloride, the resulting acid chloride solution was cooled to room temperature and was added to a solution of 100 g of N-methyl-N-(2-[4-hydroxyphenyl]ethyl) amine HBr (A12 HBr) and 94 g Na$_2$CO$_3$ in 1000 mL of MIBK and 600 mL H$_2$O pre-cooled to 0° C. A solution of NaOH (82.5 g) in 165 mL H2O was added slowly to maintain the temperature under 5° C. The reaction mixture was stirred at this temperature until TLC analysis showed the complete disappearance of B13 acid chloride. The pH of the reaction mixture was brought to 10-11 by adding more NaOH and the resulting mixture was heated to 50° C. and stirred at this temperature for another 1 h. The reaction mixture was cooled to room temperature and the aqueous layer was separated. The organic layer was concentrated to ⅕$^{th}$ of its volume. 500 mL of heptane was added. The precipitate was collected by filtration to give 163 g (65% yield) of N-methyl-N-(2-[4-hydroxyphenyl]ethyl)-2-bromo-5-hydroxy-4-methoxy benzene carboxamide (C2).

Method 3

To a solution of 138 g 2-bromo-5-hydroxy-4-methoxy benzoic acid (B13) in EA (690 mL) was added DMF (6.9 mL) and the reaction mixture was heated to 45-50° C. Thionyl chloride (120 g) was added to the solution and stirred at this temperature until TLC analysis indicated the complete disappearance of B13. The excess thionyl chloride and EA was removed by distillation at atmosphere pressure to give a liquid residue. The residue was cooled to 30° C. and was diluted with methylene chloride (690 mL) to give a B-13-Cl solution.

A separate solution of N-methyl-N-(2-[4-hydroxyphenyl]ethyl) amine (A12) was prepared by mixing A12.HBr (100 g), triethylamine (360 mL) in methylene chloride (1000 mL). To this A12 solution was added slowly the above mentioned B13-Cl solution with agitation at room temperature. The reaction mixture was stirred for another one hr at room temperature after the addition was completed. The solid precipitate was removed by filtration and the filter cake was washed with methylene chloride. The combined methylene chloride solution was distilled until the pot temperature reached 55° C. To this residue, methanol (198 g) was added. The methanol of the resulted solution was removed by distillation until the pot temperature reached 70° C. The residue was cooled to room temperature and 15% NaOH/MeOH solution (460 mL) was added. The resulting solution was stirred at room temperature for 12 hr. The reaction mixture was acidified with 36% hydrochloric acid until the pH was between 3 and 5. The solution was set for distillation until the pot temperature reached 75° C. To the residue was added methylene chloride (200 mL) and 1N HCl (1500 mL) and stirred at 0° C. for 4 hr. The precipitate was collect by filtration to give 100 g (56% yield) of N-methyl-N-(2-[4-hydroxyphenyl]ethyl)-2-bromo-5-hydroxy-4-methoxy benzene carboxamide (C2).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. It is intended, therefore, that the invention be defined by the scope of the claims which follow and that such claims be interpreted as broadly as is reasonable.

We claim:

1. A process for the preparation of a compound of Formula I:

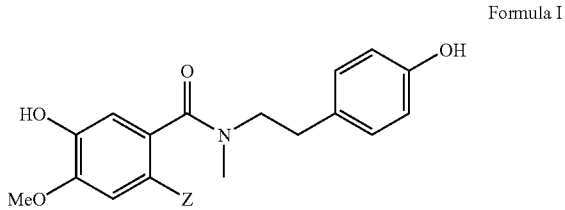

Formula I wherein Z is a blocking group,
comprising:
(1) activating a compound of the Formula II:

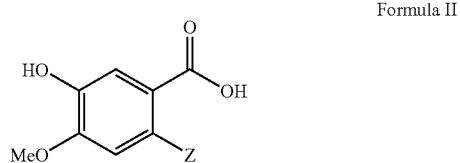

Formula II wherein Z is defined as above,
with a coupling agent to give an activated compound of the Formula III:

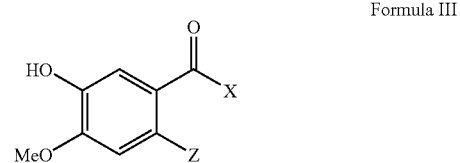

Formula III wherein X is a leaving group resulting from the use of the coupling agent; and (2) coupling the activated compound of Formula III with a compound N-methyl-N-(2-[4-hydroxyphenyl]ethyl) amine (A12) of formula:

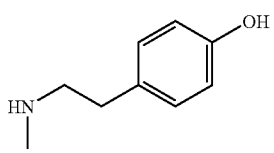

or acid salt of compound A12 to give compound of the Formula I:

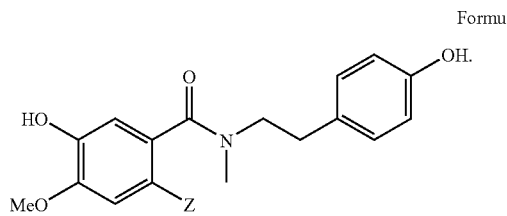

2. The process of claim 1 wherein the blocking group Z is halogen, and step (2) is carried out in the presence of a base.

3. The process of claim 1 wherein the acid salt of compound A12 is HCl or HBr salt.

4. The process of claim 1 wherein the coupling agent is selected from the group consisting a halogenating agent, trichloroacetonitrile, an optionally substituted alkyl or aryl acid halide, an optionally substituted alkyl or aryl acid halide acid anhydride, an optionally substituted alkyl or aryl alkoxide, an N-hydroxy amide, a hydroxybenzotriazole, and combinations thereof.

5. The process of claim 4 wherein the hydroxy amide is N-hydroxy succinimide (HOSU), and hydroxybenzotriazole is N-hydroxy-benzotriazole (HOBt) or 1-hydroxy-7-azabenzotriazole (HOAt).

6. The process of claim 1 wherein the leaving group is selected from the group consisting of —F, —Cl, —Br, —I, —C(NH)CCl$_3$, —O—COCF$_3$, —O—COCCl$_3$, —O—CO—R, —OR, —Osu, —OBt, and —OAt, wherein R is a substituted or unsubstituted $C_1$-$C_6$ alkyl group or a substituted or unsubstituted phenyl group.

7. The process of claim 1 wherein step (1) is carried out in an organic solvent selected from the group consisting of methylisobutyl ketone (MIBK), toluene, tetrahydrofuran (THF), diethyl ether, diglyme, methyl t-butyl ether, methylene chloride, ethyl acetate, and mixtures thereof.

8. The process of claim 1 wherein step (1) is carried out in EtOAc.

9. The process of claim 1 wherein step (1) is carried out at about 45-50° C. followed by vacuum distillation to remove the excess unreacted coupling agent.

10. The process of claim 1 wherein the coupling agent is thionyl chloride, the leaving group X in the compound of formula III is chloro, and the step (2) is carried out in the presence of a base.

11. The process of claim 1 wherein the coupling reaction is carried out in a base selected from the group consisting of an alkali hydroxide, a tertiary amine base, alkali carbonate, and combinations thereof.

12. The process of claim 11 wherein the base is sodium hydroxide.

13. The process of claim 11 wherein the base is a mixture of $Na_2CO_3$ and NaOH.

14. The process of claim 11 wherein the base is triethylamine.

15. The process of claim 1 wherein the step (2) is carried out in a solvent selected from the group consisting of methylene chloride ($CH_2Cl_2$), methanol (MeOH), ethanol (EtOH), isopropanol (IPA), MIBK, toluene, THF, diethyl ether, diglyme, methyl t-butyl ether, and mixtures thereof.

16. The process of claim 1 wherein the step (2) is carried out in a mixture of methylene chloride ($CH_2Cl_2$), methanol (MeOH), and sodium hydroxide.

17. The process of claim 1 wherein the step (2) is carried out in a two phase system comprising MIBK, and at least one of aqueous sodium bicarbonate and sodium hydroxide.

18. The process of claim 1 wherein the step (2) is carried out in methylene chloride ($CH_2Cl_2$) and triethylamine.

19. The process of claim 1 wherein the step (2) is carried out at a temperature of about 0-50° C.

20. The process of claim 1 further comprising converting the compound of formula I to (−)-galantamine.

21. A process of making (−)-galantamine comprising:

(1) activating a compound of the formula II:

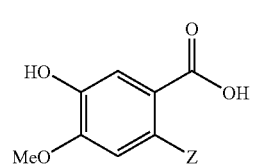

wherein Z is a blocking group, with a coupling agent to give an activated compound of the formula III:

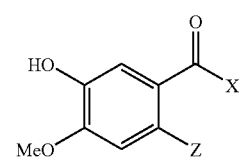

wherein X is a leaving group resulting from the use of the coupling agent; and (2) coupling the activated compound of formula III with a compound N-methyl-N-(2-[4-hydroxyphenyl]ethyl) amine (A12) of the formula:

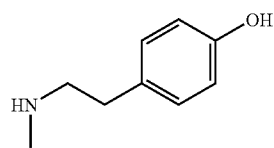

or acid salt thereof to give compound of Formula I:

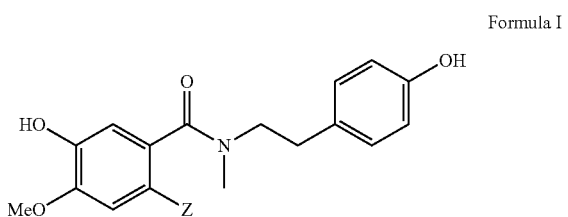

Formula I and (3) converting the compound of Formula I to (−)-galantamine.

22. The process of claim 21 wherein the coupling agent is selected from the group consisting trichloroacetonitrile, a halogenating agent, an optionally substituted alkyl or aryl acid halide, an optionally substituted alkyl or aryl acid halide acid anhydride, an optionally substituted alkyl or aryl alkoxide, an N-hydroxyl amide, an hydroxyl benzotriazole, and combinations thereof.

23. The process of claim 21 wherein the leaving group X in Formula III is selected from the group consisting of —F, —Cl, —Br, —I, —C(NH)CCl$_3$, —O—COCF$_3$, —O—COCCl$_3$, —O—CO—R, —OR, —Osu, —OBt, —OAt; wherein R is a substituted or unsubstituted C$_1$-C$_6$ alkyl group, or a substituted or unsubstituted phenyl group.

24. The process of claim 21 wherein step (1) is carried out in an organic solvent selected from the group consisting of MIBK, toluene, THF, diethyl ether, diglyme, methyl t-butyl ether, methylene chloride, ethyl acetate, and mixtures thereof.

25. The process of claim 21 wherein the step (2) is carried out in a base selected from the group consisting of an alkali hydroxide, a tertiary amine base, an alkali carbonate, and combinations thereof.

26. The process of claim 21 wherein the step (2) is carried out in a solvent selected from the group consisting of methylene chloride (CH$_2$Cl$_2$), methanol (MeOH), ethanol (EtOH), isopropanol (IPA), methylisobutyl ketone (MIBK), toluene, tetrahydrofuran (THF), diethyl ether, diglyme, and methyl t-butyl ether (MTBE), and mixtures thereof.

* * * * *